US012558454B2

(12) United States Patent
Kumta et al.

(10) Patent No.: US 12,558,454 B2
(45) Date of Patent: Feb. 24, 2026

(54) ULTRAHIGH DUCTILITY, NOVEL Mg—Li BASED ALLOYS FOR BIOMEDICAL APPLICATIONS

(71) Applicant: UNIVERSITY OF PITTSBURGH—OF THE COMMONWEALTH SYSTEM OF HIGHER EDUCATION, Pittsburgh, PA (US)

(72) Inventors: Prashant N. Kumta, Pittsburgh, PA (US); Jingyao Wu, Pittsburgh, PA (US); Oleg Velikokhatnyi, Pittsburgh, PA (US)

(73) Assignee: UNIVERSITY OF PITTSBURGH—OF THE COMMONWEALTH SYSTEM OF HIGHER EDUCATION, Pittsburgh, PA (US)

( * ) Notice: Subject to any disclaimer, the term of this patent is extended or adjusted under 35 U.S.C. 154(b) by 0 days.

(21) Appl. No.: 18/402,953

(22) Filed: Jan. 3, 2024

(65) Prior Publication Data

US 2024/0181130 A1     Jun. 6, 2024

Related U.S. Application Data

(62) Division of application No. 17/381,445, filed on Jul. 21, 2021, now Pat. No. 11,896,735, which is a division of application No. 15/532,149, filed as application No. PCT/US2015/064694 on Dec. 9, 2015, now Pat. No. 11,077,227.

(60) Provisional application No. 62/090,939, filed on Dec. 12, 2014.

(51) Int. Cl.
| | |
|---|---|
| *A61L 27/30* | (2006.01) |
| *A61L 27/04* | (2006.01) |
| *A61L 27/54* | (2006.01) |
| *A61L 31/02* | (2006.01) |
| *A61L 31/08* | (2006.01) |
| *A61L 31/16* | (2006.01) |
| *C22C 23/00* | (2006.01) |

(52) U.S. Cl.
CPC ............. *A61L 27/30* (2013.01); *A61L 27/047* (2013.01); *A61L 27/306* (2013.01); *A61L 27/54* (2013.01); *A61L 31/022* (2013.01); *A61L 31/082* (2013.01); *A61L 31/088* (2013.01); *A61L 31/16* (2013.01); *C22C 23/00* (2013.01); *A61L 2300/102* (2013.01)

(58) Field of Classification Search
CPC ....................................................... A61L 27/30
See application file for complete search history.

(56) References Cited

U.S. PATENT DOCUMENTS

| | | | |
|---|---|---|---|
| 8,435,281 B2 | 5/2013 | Weber | |
| 2002/0004060 A1 | 1/2002 | Heublein et al. | |
| 2004/0241036 A1 | 12/2004 | Meyer-Lindenberg et al. | |
| 2005/0079088 A1 | 4/2005 | Wirth et al. | |
| 2007/0191943 A1 | 8/2007 | Shrivastava et al. | |
| 2010/0249900 A1 | 9/2010 | Sager et al. | |
| 2012/0143227 A1 | 6/2012 | Steckel et al. | |
| 2013/0060326 A1 | 3/2013 | Gerold | |
| 2013/0090741 A1 | 4/2013 | Guo et al. | |
| 2014/0255952 A1 | 9/2014 | Kumta et al. | |
| 2016/0138148 A1 | 5/2016 | Schaffer et al. | |

FOREIGN PATENT DOCUMENTS

| | | |
|---|---|---|
| EP | 1997522 B1 | 5/2015 |
| WO | 2005075005 A1 | 8/2005 |
| WO | 2013052856 A3 | 4/2013 |
| WO | 2014197781 A3 | 12/2014 |

OTHER PUBLICATIONS

Leeflang et al., "Long-Term Biodegration and Associated Hydrogen Evolution of Duplex-Structured Mg—Li—Al—(Re) Alloys and Their Mechanical Properties," Materials Science and Engineering, (Aug. 6, 2011), 176(20):1741-1745.
Extended European Search Report For 15867679.1-1109 / 3229852 PCT/US2015064694, 9 pages.
Zhou et al., Mechanical Property, Biocorrosion and in Vitro Biocompatibility Evaluations 1 PF Mg—Li—(Ai)—(Re) Alloys for Future Cardiovascular Stent Application, Acta Biomaterialia, (2013), 9:8488-8498.

*Primary Examiner* — Sarah Alawadi
(74) *Attorney, Agent, or Firm* — Carol A. Marmo; Eckert Seamans Cherin & Mellott, LLC

(57) ABSTRACT

The invention includes compositions including magnesium-lithium alloys containing various alloying elements for medical implant devices. The devices are constructed of the compositions or have applied thereto a coating formed therefrom. Within the structure of the magnesium-lithium alloy, there is a co-existence of alpha and beta phases. The invention also includes methods of preparing the magnesium-lithium-based alloys and articles, such as medical implant devices, for use in medical applications, including orthopedic, dental, craniofacial and cardiovascular surgeries.

6 Claims, 3 Drawing Sheets

ULTRAHIGH DUCTILITY, NOVEL Mg—Li BASED ALLOYS FOR BIOMEDICAL APPLICATIONS

CROSS-REFERENCE TO RELATED PATENT APPLICATIONS

This patent application claims the benefit of U.S. patent application Ser. No. 17/381,445, entitled "Ultrahigh Ductility, Novel Mg—Li Based Alloys for Biomedical Applications", filed on Jul. 21, 2021, which is a Divisional Application of U.S. patent application Ser. No. 15/532,149, entitled "Ultrahigh Ductility, Novel Mg—Li Based Alloys for Biomedical Applications" filed on Jun. 1, 2017, having U.S. Pat. No. 11,077,227 and issue date of Aug. 3, 2021, which is a U.S. National Stage Application under 35 U.S.C. 371 of International Patent Application No. PCT/US2015/064694, filed Dec. 9, 2015, entitled "Ultrahigh Ductility, Novel Mg—Li Based Alloys For Biomedical Applications", which claims priority under 35 U.S.C. 119(e) to U.S. Provisional Patent Application No. 62/090,939, entitled "Ultrahigh Ductility, Novel Mg—Li Based Alloys for Biomedical Applications", filed on Dec. 12, 2014, the contents of which are incorporated herein by reference.

GOVERNMENT SUPPORT

This invention was made with government support under Grant No. EEC0812348 awarded by the National Science Foundation (NSF). The government has certain rights in the invention.

FIELD OF THE INVENTION

The present invention relates to magnesium-lithium alloy compositions, methods of preparing the alloy compositions, and uses for the alloy compositions as medical implant devices.

BACKGROUND OF THE INVENTION

Every year millions of surgical procedures are performed in the United States, which require placement of metal, e.g., stainless steel or titanium, hardware in a patient body. Implant devices, such as scaffolds, including but not limited to plates, screws, staples and sutures are commonly used in the practice of orthopedic, dental, craniofacial and cardiovascular implant surgery. In addition, implant devices and scaffolds can include endoprostheses, such as but not limited to, stents. Stents are implanted into a body of a patient to support lumens, for example, coronary arteries. An endoprosthesis is typically a tubular member that is placed in a lumen in the body. For example, the passageways, such as, arteries and other blood vessels, and other body lumens, sometimes become occluded or weakened. A passageway may be occluded by a tumor or weakened by an aneurysm. When these conditions occur, the passageway can be reopened or reinforced, or even replaced, with an implantable medical device such as an endoprosthesis. The endoprosthesis is typically introduced into the body in a compacted or reduced-size form, delivered inside the body by a catheter and transported to a target site within the body. Upon reaching the target site, the endoprosthesis is expanded so that it can contact the walls of the lumen. Furthermore, membranes are also used for guided tissue regeneration in various locations of the body to promote, e.g., favor, one tissue growth over another.

Biomaterials for the construction of implant devices are typically chosen based on their ability to withstand cyclic load-bearing and compatibility with the physiological environment of a human body. Many of these implant devices are traditionally constructed of polymer or metal. These materials of construction exhibit good biomechanical properties. Metallic biomaterials, in particular, have appropriate properties such as high strength, ductility, fracture toughness, hardness, corrosion resistance, formability, and biocompatibility to make them attractive for most load bearing applications. Polymers, such as polyhydroxy acids, polylactic acid (PLA), polyglycolic acid (PGA), and the like, are known as conventional biomaterials, however, in some instances the strength and ductility exhibited by polymers is not as attractive as that demonstrated by metallic biomaterials.

Further, there has been an interest and focus to design and develop biodegradable construction materials. There is typically a period of time after which the implant device is no longer needed, e.g., after bone or tissue healing is complete. The devices can be left in situ or, alternatively, they can be removed. Each of these alternatives has disadvantages or problems associated therewith. For example, leaving the device in situ increases the chances of infection and rejection, and removal of the device requires a second surgery and causes a risk of infection, pain and discomfort to the patient, as well as it being an additional expense. To overcome these disadvantages or problems, there has been developed a number of resorbable polymeric devices that are effective to degrade over a period of time, e.g., by dissolving in the physiological environment. Thus, the device does not remain in-situ and there is no need to surgically remove the device because when the device is no longer needed, the polymeric material degrades or dissolves within the patient body. However, there are also disadvantages associated with the resorbable polymer devices. For instance, it has been found that the resorbable polymeric materials, which are used for the construction of biodegradable medical implant devices, can lack mechanical strength as compared to that exhibited by metal implants and have a limited set of applications. As a result, there is an interest in the art to identify materials that degrade over time, while also demonstrating sufficient mechanical strength prior to degradation.

Magnesium and magnesium alloys are attractive as biomaterials for the construction of resorbable devices because they have mechanical properties compatible to bone and can be resorbed over a period of time. For example, magnesium is very lightweight, has a density similar to cortical bone, has an elastic modulus also close to natural bone, is essential to human metabolism, is a cofactor for many enzymes, and stabilizes the structures of DNA and RNA. However, there are other properties of magnesium and magnesium alloys that are problematic for their use as medical implant devices. For example, magnesium is not typically used in the fabrication of medical implant devices primarily because the corrosion of magnesium results in the production of hydrogen. Medical implant devices constructed of magnesium can cause the accumulation of hydrogen in areas surrounding the device and thus, result in the formation of gas cavities in the patient body. In order for magnesium and magnesium alloys to be considered as suitable materials for use in constructing medical implant devices, the rate of corrosion of these materials needs to be closely monitored and controlled to prevent formation of gas cavities.

In addition to corrosion problems, poor ductility of magnesium and magnesium-based alloys is a disadvantage associated with these materials that limits their application as biomedical materials, in particular, for stent applications. Medical devices, such as stents, staples and sutures, require corresponding materials that have high ductility and flexibility. Numerous technologies have been developed to control the corrosion rates of magnesium and magnesium-based alloys, such as alloying magnesium with different elements to reduce its corrosive properties, coating a magnesium or magnesium-based substrate with an anti-corrosive coating and surface modifying a magnesium or magnesium-based substrate. However, the poor ductility of magnesium and magnesium-based alloys remains an unresolved issue.

Magnesium and lithium alloys were originally developed for use in the aerospace, automotive, and aviation industries because magnesium lithium alloys are among the lightest metallic materials. Recently, application of magnesium and lithium based alloys has also expanded into the automobile, electronic products and battery industries, as well.

In the field of biomedical applications, there is a desire to develop biocompatible materials of construction for scaffolds and endoprostheses as medical implant devices wherein these devices exhibit improved mechanical properties while remaining non-toxic and maintaining their ability to degrade over time. In accordance with the invention, there is a desire to develop a magnesium-lithium alloy for scaffold and endoprostheses construction which emphasizes the beneficial properties of magnesium and also de-emphasizes its detrimental properties, such as poor ductility and low flexibility.

Thus, there is a desire in the art to develop novel magnesium-based alloys, such as magnesium and lithium alloys, for use in constructing medical implant devices, in particular, stents and sutures, which exhibit improved ductility as compared to traditional magnesium alloys known in the art. Further, the novel magnesium-based alloys should demonstrate sufficient mechanical strength for use as medical implant device and the ability to degrade over time when the medical implant device is no longer needed.

SUMMARY OF THE INVENTION

In one aspect, the present invention provides a composition for a medical implant device. The composition includes an alloy which includes magnesium and lithium. The lithium constitutes from about 5% by weight to about 11% by weight based on total weight of the alloy. The alloy is structured to exhibit a co-existence of both alpha and beta phases. The alloy can also include one or more alloying elements selected from the group consisting of iron, zirconium, manganese, calcium, yttrium, aluminum, rare earth metal elements, strontium, copper, silver, silicon, sodium, potassium, cerium and zinc. The composition can further include an active agent.

In certain embodiments, the composition is employed to form the medical implant device. In certain other embodiments, the composition is applied as a coating to a surface of the medical implant device.

In yet another aspect, the present invention provides a method for preparing a coated medical implant device. The method includes obtaining a substrate for implanting into a body, forming a coating composition comprising alloying magnesium and lithium, and applying the coating composition on a surface of the substrate to form a coating thereon. The lithium is present in an amount of about 5% by weight to about 11% by weight based on total weight of the alloy and the magnesium-lithium alloy is structured to exhibit a co-existence of alpha and beta phases.

In still another aspect, the present invention provides a medical implant device that includes an alloy which includes magnesium and lithium. The lithium constitutes from about 5% by weight to about 11% by weight based on total weight of the alloy. The alloy is structured to exhibit a co-existence of both alpha and beta phases. The medical implant device can contain the alloying elements above-described to exhibit high ductility and corrosion resistance acceptable for implantation of the medical device. The medical implant device can have plasticity and ductility that exceeds the plasticity and ductility of conventional magnesium or magnesium-based alloy devices. The medical implant device can be effective for use in orthopedic, dental, craniofacial and cardiovascular surgeries. The medical implant device can be effective to release lithium ions as a therapeutic drug eluting device.

BRIEF DESCRIPTION OF THE DRAWINGS

In general.

FIG. 2(a) is a plot showing yield strength and ultimate tensile strength;

FIG. 2(b) is a plot showing elongation; and

DETAILED DESCRIPTION OF THE INVENTION

Figure 1:
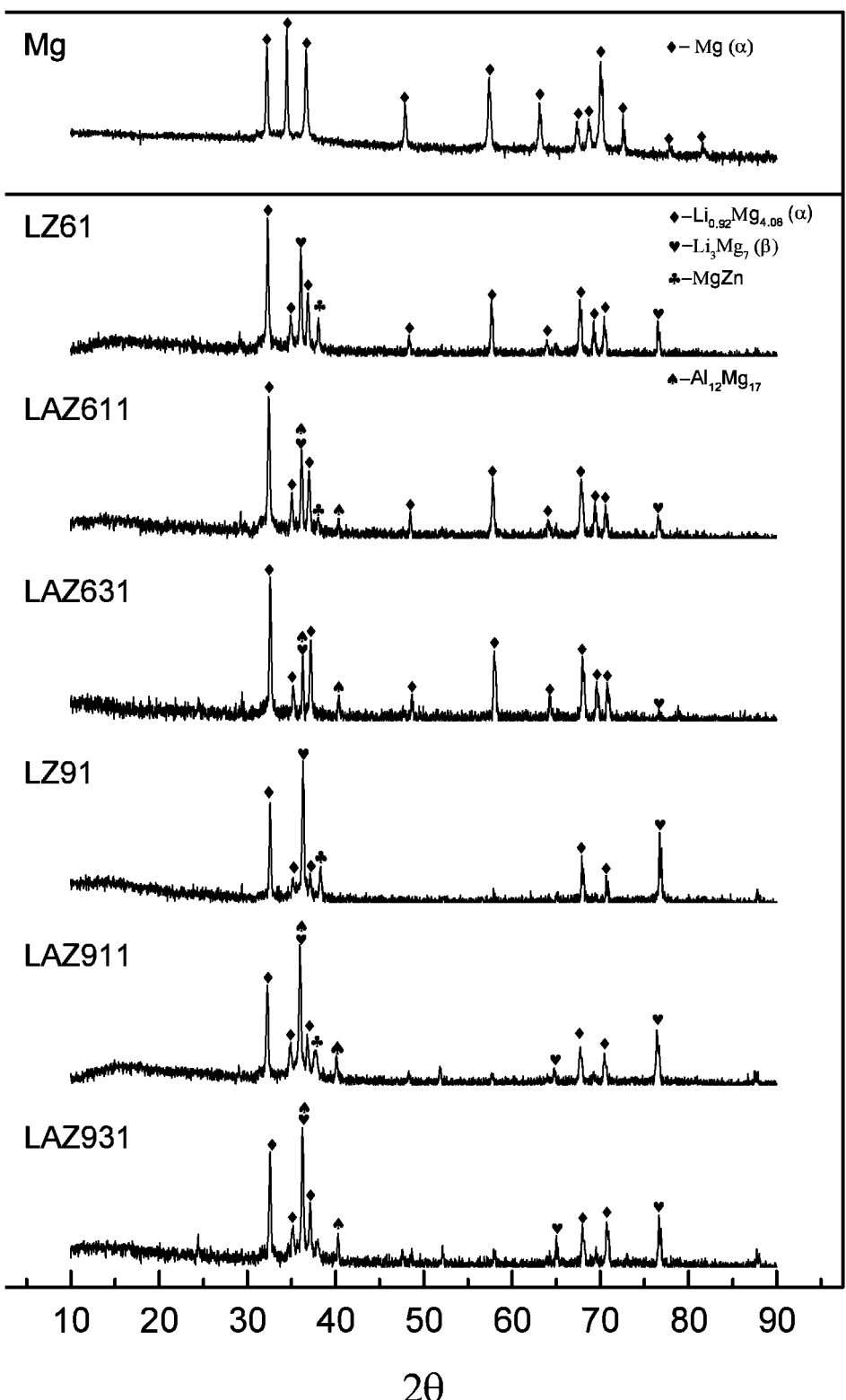
FIG. 1 shows X-ray diffraction patterns of fabricated Mg—Li alloys in accordance with certain embodiments of the invention, compared to the XRD pattern of pure Mg.

The invention relates to novel, biocompatible, biodegradable magnesium-lithium alloys. Further, the invention relates to articles, such as medical devices for implantation into a body of a patient, which include the magnesium-lithium alloys. Compositions including the magnesium-lithium alloys can be used to construct or fabricate medical implant devices or at least a portion of medical implant devices. Furthermore, the magnesium-lithium alloy can be present in a coating composition for at least partial application or deposition on a surface of a medical implant device to form a coating or layer thereon. Moreover, the invention relates to methods of preparing the magnesium-lithium alloys and articles, such as medical implant devices, for use in medical applications, such as but not limited to, orthopedic, dental, craniofacial and cardiovascular surgery.

The magnesium-lithium alloys in accordance with the invention are effective to modify various properties and characteristics of pure magnesium, such as, but not limited to, the poor ductility that is traditionally associated with elemental magnesium. Without intending to be bound by any particular theory, it is believed that the presence of lithium in the alloy improves the mechanical properties associated with the medical implant devices produced therefrom. For example, medical implant devices constructed from known magnesium-containing alloys (in the absence of lithium) can have poor mechanical properties, such as, low flexibility and as-aforementioned poor ductility. The magnesium-lithium alloys have enhanced mechanical properties and therefore, medical implant devices constructed therefrom, such as, but not limited to vascular stents, can demonstrate enhanced flexibility, e.g., plasticity, and ductility.

Traditional magnesium alloys have a hexagonal close packed (HCP) structure, which is commonly referred to as an alpha phase. However, when magnesium-lithium alloys have a lithium content that is equal to or exceeds about 5% by weight based on total weight of the alloy, a beta phase with body-centered cubic (BCC) structure forms and co-exists with the alpha phase. As the lithium content of the alloy increases, the alpha phase diminishes and may be at least partially replaced and in some embodiments, completely replaced, by the beta phase. For example, when the lithium content is about 11 percent by weight or greater, based on the total weight of the alloy, the alpha phase is essentially completely replaced with the beta phase. Without intending to be bound by any particular theory, it is believed that a dual phase structure, e.g., co-existence of alpha and beta phases in the magnesium-lithium alloy, can result in significantly enhanced elasticity and ductility. Further, it is believed that these unique properties are attributed to a decrease in the lattice constant ratio (e.g., c/a) as the lithium content increases, activating non-basal slip planes and resulting in a significant increase in the volume fraction of the BCC phase.

Thus, in certain embodiments, lithium can be present in an amount from about 5%, or greater than about 5%, by weight to about 11%, or at least about 11%, by weight based on the total weight of the alloy.

In certain embodiments, the magnesium-lithium alloys can include one or more other elemental alloy components, such as, but not limited to, iron, zirconium, manganese, calcium, yttrium, rare earth elements, and zinc. The amount of each of the components can vary and, in general, the amounts are selected such that the resulting magnesium-lithium alloys are within acceptable non-toxic limits, sufficiently biocompatible and degradable over a period of time. Further, as aforementioned, the amount of the lithium is such that the alpha phase is at least partially replaced with the beta phase to produce enhanced flexibility and ductility as compared to traditional magnesium alloys.

It is contemplated that other components, in addition to the magnesium-lithium alloy, may be added to the compositions according to the invention, provided that the non-toxicity, biocompatibility and degradability remain within acceptable limits. Acceptable non-toxic limits and time frames for degradation can vary and may depend on the particular physical and physiological characteristics of the patient, in vitro site of implantation and medical use of the device. Non-limiting examples of suitable other components for use in the magnesium-lithium alloy or compositions according to the invention include aluminum, strontium, copper silver, silicon, sodium, potassium, cerium, other rare earth elements and, combinations and mixtures thereof.

In general, the magnesium-lithium alloys of the invention can be formed using known apparatus and conventional alloying techniques. In certain embodiments, the metal elements of the compositions are alloyed by employing high energy mechanical alloying (HEMA) and uniaxial or iso-static compaction and sintering. In general, pressing, sintering and casting methods can be employed to construct medical implant devices. It is believed that the particular process used for casting may affect the properties and characteristics of the cast composition. In certain embodiments, the casting may be performed under a protective atmosphere to preclude, minimize or reduce decomposition of the components in the composition. In particular, it may be desirable to preclude, minimize or reduce the decomposition of magnesium in the composition. The protective atmosphere can include compounds selected from those known in the art, such as but not limited to, argon, sulfur hexafluoride and mixtures thereof. In further embodiments, the resulting cast can be subjected to various forming and finishing processes known in the art. Non-limiting examples of such processes include, but are not limited to, extrusion, forging, polishing (by mechanical and/or chemical means), surface treating (to form a superficial layer on the surface), and combinations thereof. The resulting cast structure can be formed, finished, machined and manipulated to produce articles and devices for use in medical applications. As previously described, the magnesium-lithium alloys of the invention can be used to produce various articles, such as medical devices suitable for implantation into a body of a patient and, in preferred embodiments, the medical implant devices include orthopedic, craniofacial and cardiovascular devices.

The magnesium-lithium alloy-containing compositions and devices described herein can include at least one active agent or substance. In certain embodiments, the active substance is incorporated within the composition containing the alloy material. The composition then can be used to form or construct a medical implant device, or the composition can be used to apply or deposit a coating on the surface of an existing medical implant device. Alternatively, the active substance can be applied to the surface of a medical implant device that is constructed of, or coated with, the magnesium-lithium alloy. Further, the active substance can be incorporated into pores formed in the medical implant device itself. As used herein, the term "active substance" and related terms refer to a molecule, compound, complex, adduct and/or composite that exhibits one or more beneficial activities, such as, therapeutic activity, diagnostic activity, biocompatibility, corrosion, and the like. Active substances that exhibit a therapeutic activity can include bioactive agents, pharmaceutically active agents, drugs and the like. Non-limiting examples of bioactive agents include, but are not limited to, bone growth promoting agents, such as growth factors, drugs, proteins, antibiotics, antibodies, ligands, DNA, RNA, peptides, enzymes, vitamins, cells and the like, and combinations thereof. In certain embodiments, the magnesium-lithium alloys of the invention can be modified via covalent bonding with different molecules, including bioactive molecules, such as proteins and peptides. These chemistry modifications can provide the ability to control different physical chemical properties of the alloys, including but not limited to, hydrophobicity and charge, as well as bioactivity.

The implantable medical devices constructed of, or coated with, the magnesium-lithium alloys of the invention can be effective for tissue regeneration and bone regeneration within a body of a patient. Non-limiting examples of suitable implantable medical devices include, but are not limited to, scaffolds, plates, meshes, staples, screws, pins, tacks, rods, suture anchors, tubular mesh, coils, x-ray markers, catheters, endoprostheses, pipes, shields, bolts, clips or plugs, dental implants or devices, such as but not limited to occlusive barrier membranes, graft devices, bone-fracture healing devices, bone replacement devices, join replacement devices, tissue regeneration devices, cardiovascular stents and sutures, nerve guides, surgical implants and wires.

There are described herein various embodiments of the invention wherein the magnesium-lithium alloys are employed as materials of construction for scaffolds or structures as medical implant devices. In these embodiments, the magnesium-lithium alloys can make up the entire structure of only a portion or part of the structure. As described herein, the present invention includes the use of the magnesium-lithium alloys to form or construct structures for implantation. Further, the present invention includes the use of magnesium-lithium alloys to form coating compositions and, the coating compositions can be applied to at least a portion of a surface of a scaffold or structure of a medical implant device. Application of the coating can be accomplished using a wide variety of conventional coating techniques known in the art, including but not limited to, spraying, wiping, brushing, dipping, chemical vapor deposition, e.g., vapor sputtering, and the like. Furthermore, the magnesium-lithium coating compositions can be directly applied to the surface of the structure or, alternatively, the surface of the structure can be pretreated prior to applying the magnesium-lithium coating. Pretreatment of the structure can include applying an intermediate coating to the surface of the structure in order to enhance adherence of the magnesium-lithium coating. As aforementioned, the magnesium-lithium compositions for constructing and/or coating the medical implant device can also include the presence of an active substance.

Moreover, since lithium can inhibit proliferation of vascular smooth muscle cells, it is contemplated that the magnesium-lithium alloy of the invention can be used to form a medical implant device, which can alone or individually serve as a drug or active agent eluting stent.

The magnesium-lithium alloys in accordance with the invention have numerous advantages as compared to conventional magnesium alloys, including, but not limited to, for example, tunability or control. That is, the mechanical properties and degradation rate of the magnesium-lithium alloy can be tuned or controlled by adjusting the content of lithium present in the alloy. Further advantages include, but are not limited to, one or more of the following:

Capability to provide mechanical support and to gradually degrade as damaged tissue heals and remodels;

Improved strength;

Ease of processing (e.g., extrusion and ECAP) at relatively low temperature;

Comparable corrosion rate to known magnesium alloys;

No local and systematic toxicity; and

Non-interference with current clinical image systems, such as, MRI and X-ray.

EXAMPLES

Magnesium-lithium-zinc-(aluminum) alloys were fabricated. The alloys were melted and casted under high vacuum conditions, followed by heat treatment and extrusion. The composition of the alloys is listed in Table 1. The co-existence of dual phases (alpha and beta phases) of the fabricated magnesium-lithium-zinc-(aluminum) alloys was verified by the X-ray patterns, as shown in FIG. 1. Pure magnesium consists of a single alpha (α) phase. However, in all magnesium-lithium-zinc-(aluminum) alloys fabricated, the peaks representing alpha (α) phase or beta (β) phase are both exhibited in X-ray patterns of the corresponding alloys. The corrosion rate and cyto-compatibility were evaluated in vitro. Overall biocompatibility and in vivo degradation rate were also assessed in animal models.

Figure 2A:
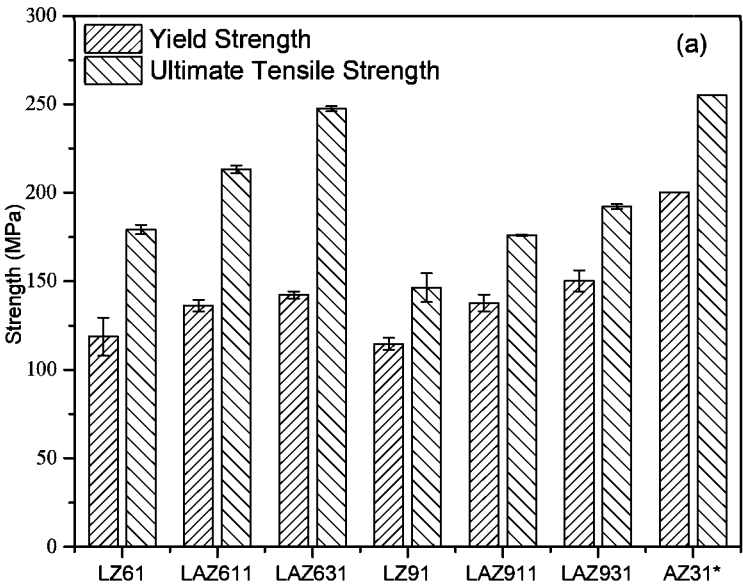
FIG. 2(a) and FIG. 2(b), show the mechanical properties of magnesium-lithium alloys in accordance with certain embodiments of the invention, compared to known magnesium alloys.
Figure 2B:
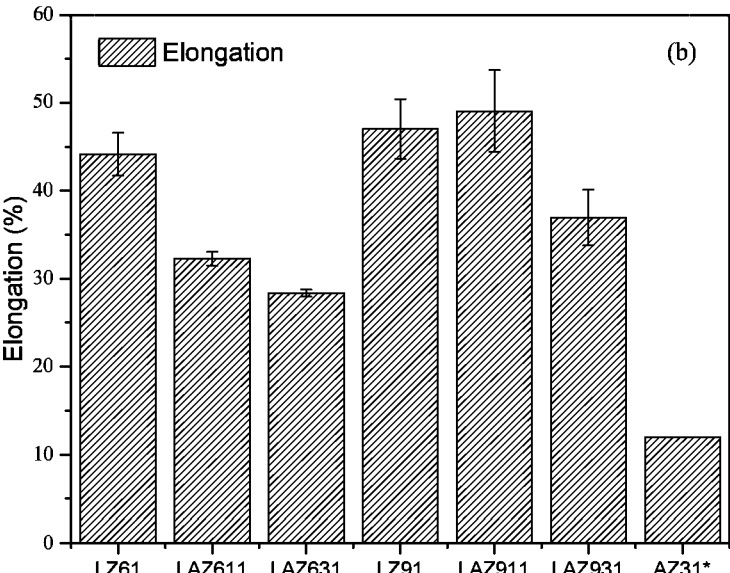

The following mechanical properties of the fabricated alloys were tested and evaluated: yield strength, ultimate tensile strength and elongation at fracture. The results are shown in FIG. 2(*a*) and FIG. 2(*b*). As shown in FIG. 2(*a*), for some compositions of Mg—Li alloys in accordance with the invention, such as LAZ631, the ultimate tensile strength was almost the same as AZ31 (a magnesium alloy, i.e., absent lithium, which is widely known and commercially available). The yield strength was generally lower than AZ31 (which was considered advantageous). Lower yield strength can be a benefit in constructing medical devices that require a certain amount of plastic deformation. For example, in stent applications, in particular, lower yield strength may enable fabrication of stents that can be easily expanded and therefore, delivery of the stents may be significantly simplified. As shown in FIG. 2(*b*), AZ31 alloy demonstrated moderate ductility as compared to other commercially available magnesium alloys. The Mg—Li alloys in accordance with the invention demonstrated ductility that was two to three times higher than the moderate ductility demonstrated by AZ31.

TABLE 1

The chemical composition (in weight percent) of Mg-Li alloys.

| Alloy | Li | Al | Zn | Mg |
|---|---|---|---|---|
| LZ61 | 6.11 ± 0.13% | 0.04 ± 0.06% | 0.92 ± 0.08% | Bal. |
| LAZ611 | 5.87 ± 0.12% | 1.10 ± 0.02% | 0.74 ± 0.05% | Bal. |
| LAZ631 | 5.90 ± 0.15% | 3.32 ± 0.13% | 0.89 ± 0.05% | Bal. |
| LZ91 | 9.00 ± 0.14% | 0.01 ± 0.01% | 0.96 ± 0.04% | Bal. |
| LAZ911 | 8.99 ± 0.13% | 1.07 ± 0.02% | 0.87 ± 0.06% | Bal. |
| LAZ931 | 9.37 ± 0.07% | 3.30 ± 0.10% | 0.87 ± 0.06% | Bal. |

Theoretical calculations were then performed to assess the results obtained (as shown in FIG. 2(*a*) and FIG. 2(*b*)) for the fabricated Mg—Li alloys identified in Table 1. The alloy compositions for the theoretical calculations are shown in Table 2. Further, Table 2 includes the calculated results, which demonstrate the high ductility of Li-containing Mg alloys as reflected by the B/G ratio of the bulk and shear moduli, which is much higher than that for pure elemental Mg. These results support the results obtained for the fabricated Mg—Li alloys.

TABLE 2

Calculated elastic constants $C_{ij}$ and different modules for pure Mg and Mg—Li alloys (in GPa)
$\overline{C_{11}} = (C_{11} + C_{22} + C_{33})/3; \overline{C_{12}} = (C_{12} + C_{13} + C_{23})/3; \overline{C_{44}} = (C_{44} + C_{55} + C_{66})/3$

| Alloy | $\overline{C_{11}}$ | $\overline{C_{12}}$ | $\overline{C_{44}}$ | B Bulk | G Shear | E Young's | v Poison's ratio | B/G |
|---|---|---|---|---|---|---|---|---|
| Mg | 61.2 | 22.5 | 17.3 | 35.4 | 18.1 | 46.5 | 0.28 | 1.96 |
| Mg—Li$_{0.03}$ (0.8 wt % Li) | 57.8 | 24.8 | 17.8 | 35.8 | 17.3 | 44.7 | 0.29 | 2.07 |
| Mg—Li$_{0.08}$ (2.5 wt % Li) | 55.4 | 26.4 | 18.3 | 36.1 | 16.8 | 43.6 | 0.30 | 2.15 |

TABLE 2-continued

| | | | | B | G | E | v | |
|---|---|---|---|---|---|---|---|---|
| Alloy | $\overline{C_{11}}$ | $\overline{C_{12}}$ | $\overline{C_{44}}$ | Bulk | Shear | Young's | Poison's ratio | B/G |
| Mg—Li$_{0.25}$ (8.7 wt % Li) | 53.3 | 26.3 | 15.3 | 35.3 | 14.6 | 38.5 | 0.32 | 2.41 |
| Mg—Li$_{0.33}$ (12.5 wt % Li) | 51.6 | 24.9 | 14.1 | 33.8 | 13.8 | 36.4 | 0.32 | 2.45 |

Figure 3:
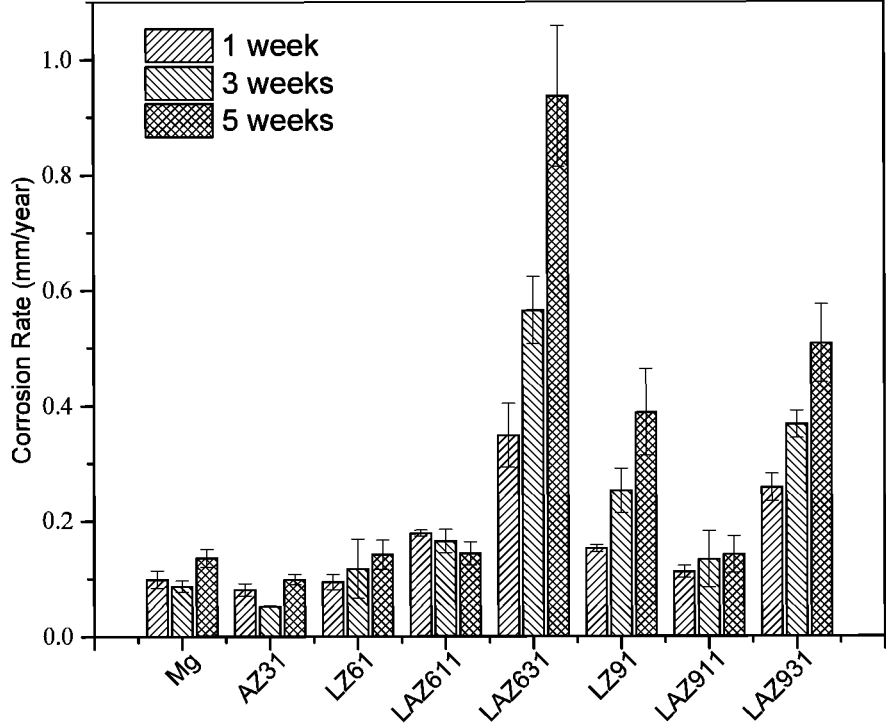
FIG. 3 is a plot showing corrosion rates of magnesium-lithium alloys in accordance with certain embodiments of the invention, compared to known magnesium alloys.

Calculated elastic constants $C_{ij}$ and different modules for pure Mg and Mg—Li alloys (in GPa) $\overline{C_{11}} = (C_{11} + C_{22} + C_{33})/3$; $\overline{C_{12}} = (C_{12} + C_{13} + C_{23})/3$; $\overline{C_{44}} = (C_{44} + C_{55} + C_{66})/3$ The fabricated Mg—Li alloys identified in Table 1 were then subjected to 1, 3 and 5-week immersion tests in Hank's solution. The results of this cumulative study are shown in FIG. 3. As shown in FIG. 3, after one week of immersion, the corrosion rate for LAZ911 was lowest; and similar to the corrosion rate for AZ31. For some alloys, such as LZ61 and LZ91, the corrosion was also comparable to elemental Mg, although, higher than AZ31. Longer immersion test results showed that LZ61, LAZ611 and LAZ911 exhibited similar corrosion rates, which were, however, slightly higher than AZ31 alloys. The corrosion rates are reflective of loss of the alloy excluding the formation of a passivation layer that is biocompatible and serving as a protective layer over the alloy.

It was noted that it would be inappropriate to evaluate overall degradation behavior of the Mg—Li alloys based on a 7-day corrosion test and data obtained therefrom. Longer immersion testing provided a more complete view of the in vitro degradation profile for the alloys. As shown, the 5-week immersion result displayed in FIG. 3 shows the comparable corrosion rate of LAZ611, LAZ911 and LZ61 to pure Mg while being slightly higher than AZ31.

Further, Li is known to inhibit the proliferation of vascular smooth muscle cells (VSMCs). Hence, the alloys in the invention with the release of Li can serve the dual purpose of providing the desired mechanical properties as well as a drug eluting device in the absence of any coatings.

It will be appreciated by those skilled in the art that changes could be made to the embodiments described above without departing from the broad inventive concept thereof. It is understood, therefore, that this invention is not limited to the particular embodiments disclosed, but it is intended to cover modifications that are within the spirit and scope of the invention.

The invention claimed is:

1. A method for preparing a coated medical implant device, comprising:
   obtaining a substrate structured for implanting into a body;
   forming a coating composition comprising:
   forming an alloy, comprising:
      I alloying about 9.0% by weight of lithium, 0.96% by weight of zinc, and 0.01% by weight of aluminum, and a remainder of magnesium based on the total weight of the alloy, or
      II alloying about 8.99% by weight of lithium, 0.87% by weight zinc, and 1.07% by weight aluminum, and a remainder of magnesium based on the total weight of the alloy, or
      III alloying about 6.11% by weight of lithium, 0.92% by weight zinc, and 0.04% by weight aluminum, and a remainder of magnesium based on the total weight of the alloy,
      wherein the alloy of I, II or III is structured to exhibit a co-existence of alpha and beta phases, and
      wherein the alloy of I, II or III exhibits one or more of improved ductility and elasticity; and
   applying the coating composition onto a surface of the substrate to form a coating thereon.

2. The method of claim 1, wherein the alloying step further comprises adding to I, II or III one or more alloying elements selected from the group consisting of iron, zirconium, manganese, calcium, yttrium, rare earth elements, strontium, copper, silver, silicon, sodium, potassium, and cerium.

3. The method of claim 1, further comprising adding an active agent to the coating composition.

4. The method of claim 1, further comprising using the coated medical implant device in orthopedic, dental, craniofacial and cardiovascular surgeries.

5. The method of claim 1, wherein the coated medical implant device releases lithium ions as a therapeutic drug eluting device.

6. The method of claim 1, wherein the alloying step comprises:
   high energy mechanical alloying of I, II or III alloy compositions;
   followed by uniaxial or isostatic compaction; and
   followed by sintering.

* * * * *